United States Patent
Haddad et al.

(10) Patent No.: US 7,101,621 B2
(45) Date of Patent: Sep. 5, 2006

(54) AZLACTONE-FUNCTIONAL HYDROPHILIC COATINGS AND HYDROGELS

(75) Inventors: Louis C. Haddad, Mendota Heights, MN (US); James I. Hembre, Plymouth, MN (US); Jerald K. Rasmussen, Stillwater, MN (US); Daniel Sarpong, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 137 days.

(21) Appl. No.: 10/896,664

(22) Filed: Jul. 22, 2004

(65) Prior Publication Data

US 2005/0003198 A1    Jan. 6, 2005

Related U.S. Application Data

(62) Division of application No. 09/860,944, filed on May 18, 2001, now Pat. No. 6,794,458.

(51) Int. Cl.
*B32B 27/00* (2006.01)
*B32B 27/02* (2006.01)
*B32B 27/08* (2006.01)

(52) U.S. Cl. ............... 428/357; 428/364; 428/402; 428/447; 428/500; 428/689; 428/411.1; 526/260

(58) Field of Classification Search ............... 428/447, 428/500, 609, 411.1, 357, 364, 402; 526/260
See application file for complete search history.

(56) References Cited

U.S. PATENT DOCUMENTS 3,488,327 A    1/1970    Kollinsky et al.
3,583,950 A    6/1971    Kollinsky et al.
3,598,790 A    8/1971    Kollinsky et al.
4,304,705 A    12/1981   Heilmann et al.
4,451,619 A    5/1984    Heilmann et al.
4,485,236 A    11/1984   Rasmussen et al.
5,149,806 A    9/1992    Moren et al.
5,204,219 A    4/1993    Van Ooij et al.
5,292,840 A    3/1994    Heilmann et al.
5,344,701 A    9/1994    Gagnon et al.
5,436,147 A    7/1995    Pegg et al.
5,464,900 A    11/1995   Stofko, Jr. et al.
5,500,251 A    3/1996    Burgoyne, Jr. et al.
5,602,202 A    2/1997    Groves
5,639,546 A    6/1997    Bilkadi
6,156,478 A *  12/2000   Liu et al. .................. 430/270.1

FOREIGN PATENT DOCUMENTS

DE    1 936 155     2/1971
WO    WO 98/28026   7/1998
WO    WO 99/53319   10/1999
WO    WO 00/26725   5/2000
WO    WO 01/16370   3/2001

* cited by examiner

*Primary Examiner*—Ana Woodward
(74) *Attorney, Agent, or Firm*—Jean A. Lown; Christopher D. Gram

(57) ABSTRACT

Surface coatings including azlactone-functional hydrogels and articles with the coatings disposed thereon are disclosed. Methods of making the coating and controlling the gellation time of the hydrogels are also disclosed.

22 Claims, No Drawings

AZLACTONE-FUNCTIONAL HYDROPHILIC COATINGS AND HYDROGELS

CROSS REFERENCE TO RELATED APPLICATIONS

This application is a division of U.S. patent application Ser. No. 09/860,944, filed May 18, 2001, now U.S. Pat. No. 6,794,458.

FIELD OF THE INVENTION

This invention relates to porous, hydrogel coatings useful for the immobilization of biologically active molecules and, particularly, to crosslinked, azlactone-functional hydrogel coatings that are useful for the preparation of DNA and protein arrays, diagnostic devices and materials for the separation of biological species. More particularly, this invention relates to porous hydrophilic, crosslinked, azlactone-functional coatings and gels.

BACKGROUND

Coatings derived from copolymers of polymerizable azlactones and olefinically unsaturated monomers are known. Such coatings are derived, in general, from rigid, high glass transition temperature ($T_g$), hydrophobic copolymers. Crosslinking is accomplished by dispersing or dissolving the azlactone copolymer with a crosslinking agent, generally in an approximately stoichiometric amount to the azlactone, in a volatile organic liquid, applying the mixture to a substrate, then allowing the coating to crosslink via azlactone ring-opening reactions with the crosslinking agent. Suitable crosslinkers are polyols and polyamines. Polyamines, such as ethylene diamine, react with azlactones at room temperature, thereby forming crosslinks. Because of the rapid reaction between azlactones and primary amines, incorporation of a ketone solvent in the coating mixture is desirable. Polyols react much slower with azlactones and generally require a catalyst, such as a strongly acidic or basic catalyst, to promote crosslinking.

Various coatings derived from azlactone copolymers are known. For example, known coatings include copolymers of 2-alkenylazlactones with acrylic acid esters and copolymerizable vinylidene compounds having at least one hydroxyl group that crosslink on drying or mild heating. Such polymers crosslink by reaction of the hydroxyl groups on one chain of the polymer with azlactone groups on other chains. In general, an acidic or basic catalyst is again needed to facilitate the crosslinking reaction. Coatings derived from azlactone copolymers that are crosslinkable by exposure to radiation are useful in imaging applications. Uncrosslinked azlactone copolymers may be used to coat a variety of substrates. These coated substrates can be used for the immobilization of functional materials, including biologically active species such as proteins. Crosslinked azlactone-functional moieties may be included in a coating over the surfaces of chemically reactive, porous supports. These reactive supports can, in turn, be reacted with biologically active materials to produce adduct supports.

While there are a variety of methods for producing coatings derived from azlactone-functional materials, some of which provide azlactone-functional coatings useful for the immobilization of other species, there remains a need for additional or improved methods for providing coated materials for use in the immobilization of biologically active materials.

SUMMARY

This invention relates to the preparation of reactive hydrophilic coatings and hydrogels that can be applied to various substrates for the purpose of covalently attaching a functional material to the substrate. In particular, the invention provides a crosslinked hydrogel for coating a substrate comprising at least one azlactone-functional copolymer comprising a plurality of azlactone moieties, a plurality of azlactone functional groups, and at least one comonomer, and at least one crosslinker comprising a first moiety and a second moiety, wherein the first moiety of a first crosslinker is covalently bound to a first azlactone moiety and the second moiety of the first crosslinker is covalently bound to a second azlactone moiety or a second crosslinker.

In some embodiments of the crosslinked hydrogel of the present invention, the second moiety of the first crosslinker is covalently bound to a second azlactone moiety. In such embodiments, the first crosslinker may be a primary polyamine, a polyether polyamine, a compound containing both a primary and a secondary amine, or any other suitable crosslinker. In other embodiments, the second moiety of the first crosslinker is covalently bound to a second crosslinker molecule. In such embodiments, the first crosslinker may be bound to a second crosslinker molecule having the same chemical structure as the first crosslinker. Alternatively, the first crosslinker may be bound to a second crosslinker having a different chemical structure than the first crosslinker. In either embodiment described above, the first crosslinker, the second crosslinker, or both may be a heterobifunctional crosslinker such as an aminoalkylalkoxysilane.

In some embodiments of the present invention, the crosslinked hydrogel includes polymers made from ionic or non-hydrophilic comonomers.

DETAILED DESCRIPTION OF THE INVENTION

This invention relates to the preparation of reactive hydrophilic coatings and hydrogels that can be placed on the surfaces of various substrates or within the structures of various structured (i.e., macro- or microstructured) substrates for the purpose of covalently attaching a functional material to the substrate. More specifically, the present invention provides compositions and processes for applying coatings including azlactone functionality onto substrate surfaces. The coatings may include thin films, thick gels, or any intermediate thickness. These coatings may provide for the attachment of functional materials to the substrate. A "functional material" is any chemical species having (a) a nucleophilic group that can react with an azlactone and (b) another reactive site, which is desired to be attached to the substrate to accomplish a specific purpose. In certain embodiments of the present invention, the functional material includes a biologically active material.

For the purposes of this invention, the following definitions shall have the meanings set forth.

"1°/2° amine-containing compound" as used herein shall mean any compound, molecule, composition or complex having one primary amine-containing functional group and at least one secondary amine-containing functional group.

"Azlactone functional group" shall mean a functional group having the structure:

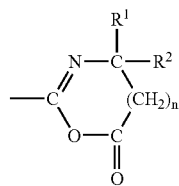

wherein $R^1$ and $R^2$ are, independently, an alkyl group having 1–14 carbon atoms, a cycloalkyl group having 3–14 carbon atoms, an aryl group having 5–12 ring atoms, an arenyl group having 6–26 carbon atoms and 0–3 S, N, or nonperoxidic O atoms, or $R^1$ and $R^2$ taken together with the carbon to which they are both joined form a carbocyclic ring having 4–12 carbons, and n is the integer 0 or 1.

"Functional group" as used herein shall mean a combination of atoms in a molecule, compound, composition or complex that tends to function as a single chemical entity. Examples of functional groups include, but are not limited to, —$NH_2$ (amine), —COOH (carboxyl), siloxane, —OH (hydroxyl), and azlactone. For example, prior to reaction, certain crosslinkers may contain one or more amine functional groups and certain copolymers may contain one or more azlactone functional groups.

"Heterobifunctional" as used herein shall mean, with respect to any molecule, compound, composition or complex, having more than one functional group and having at least two functional groups that are different from one another. For example, an amino acid is heterobifunctional because it contains two functional groups, the amino group and the carboxyl group, that are different than one another.

"Hydrogel" means a water-containing gel, i.e., a polymer that is hydrophilic and will absorb water, yet is insoluble in water.

"Ionic," with respect to monomers, shall be construed broadly to refer to monomers that inherently have a formal charge as well as monomers that are acidic or basic enough that they can acquire a formal charge when in contact with an aqueous medium.

"Moiety" as used herein shall mean the portion of a functional group from a first reactant that combines with a functional group of a second reactant to form a covalent bond in the reaction product. For example, in a peptide bond, the —NH— that participates in the peptide bond remains from the amine functional group of one amino acid and is therefore considered, herein, to be an amine moiety in the peptide product. The —C=O that participates in the peptide bond remains from the carboxylic acid functional group of the second amino acid and is therefore considered a carboxyl moiety in the peptide product.

"Non-hydrophilic" as used herein shall refer, with respect to any molecule, compound, composition or complex, to any material that has a Hydrophilicty Index of less than about 40.

"Pot life" shall mean the length of time during which a coating formulation remains soluble and homogeneous with low attendant viscosity.

"Primer" shall mean any suitable material that promotes or improves adhesion between the copolymer and the substrate. "Primer" shall include both inert primers and reactive primers. Inert primers act as an adhesion-promoting interlayer between the copolymer and the substrate. Reactive primers form covalent bonds between the copolymer and the substrate to improve adhesion.

The azlactone-functional hydrogel coatings of the present invention are produced by first preparing a solution of a hydrophilic, azlactone-functional copolymer. This copolymer is then formulated with an appropriate crosslinker, and the mixture is then coated on or applied to an appropriate substrate. The crosslinker reacts with a portion of the azlactone groups of the copolymer, thereby forming the porous, crosslinked hydrogel. Unreacted azlactone groups in the hydrogel coating are then available for the attachment of fictional materials for the appropriate end uses.

Azlactone-functional copolymers may be prepared by a variety of free radical polymerization processes in which alkenyl azlactone monomers are copolymerized with comonomers. Typical solution polymerization processes have been reported, for example, in U.S. Pat. No. 4,304,705, issued to Heilmann et al. and U.S. Pat. No. 3,583,950, issued to Kollinsky et al. For the purposes of this invention, suitable comonomers include, without limitation, hydrophilic or water-soluble monomers such as acrylamide, methacrylamide, N-mono- and N,N-disubstituted acrylamides and methacrylamides, N-vinylamides such as N-vinylformamide and N-vinylpyrrolidinone, and hydroxyalkylacrylates and acrylamides such as 2-hydroxyethylmethacrylate and N-acryloyl-trishydroxymethylaminomethane. For many applications, uncharged copolymers may be desirable in order to reduce the possibility for nonspecific binding of biological macromolecules to the coatings. For specific applications, however, ionic comonomers may also be incorporated into the copolymers. Ionic monomers may be anionic or cationic. Anionic monomers include unsaturated acids and their metal salts, such as acrylic, methacrylic, maleic, fumaric, and itaconic acids, vinyl phosphoric and phosphonic acids, styrenesulfonic acid, and 2-acrylamido-2-methyl-1-propanesulfonic acid; cationic monomers include amine-containing monomers such as 2-, 3- or 4-vinylpyridine, (3-acrylamidopropyl)trimethylammonium chloride, 2-diethylaminoethylacrylate and methacrylate, 3-dimethylaminopropylacrylate and methacrylate, and similarly substituted acrylamides and methacrylamides.

Copolymers within the scope of this invention also may include non-hydrophilic comonomers. As used herein, non-hydrophilic comonomers include any comonomer that has a Hydrophilicity Index of less than about 40. The Hydrophilicity Index (or "H.I.") is an empirical concept that may be useful for describing the hydrophilic character of monomers suitable for use in the present invention. H.I. is defined as:

H.I.=total molecular weight of all hydrophilic groups in the monomer/molecular weight of the monomer×100. molecular weight of the monomer Hydrophilic groups are generally those that are functionally capable of forming hydrogen bonds with water. Examples of hydrophilic groups include, but are not limited to, —N—, —NH—, —$NH_2$—, —O—, —OH, —COOH, —C=O, —OC=O, —$CO_2^-M^+$ (wherein $M^+$ is an alkali or alkaline earth metal cation), —SH, $SO_3H$, —$SO_3^-M^+$, —NHCONH—, and other ionic functional groups.

Non-hydrophilic comonomers may be incorporated at less than about 50% by weight and still maintain sufficient hydrophilicity of the coatings and help minimize nonspecific binding. Certain embodiments incorporate non-hydrophilic comonomers at less than about 30% by weight. Suitable non-hydrophilic comonomers include, without limitation, known acrylate and methacrylate esters, styrene, and other free radically polymerizable monomers.

Once the appropriate azlactone-functional copolymer has been prepared, coating mixtures are formulated by adding crosslinkers to the copolymer. This is conveniently done in an appropriate organic solvent that is nonreactive with azlactone functional groups. The copolymer may be diluted with solvent to a concentration of about 5% by weight or less prior to the addition of crosslinker. In other embodiments, the copolymer may be diluted with solvent to concentrations of about 10% by weight or about 20% by weight prior to the addition of crosslinker. The solvent used for dilution may be the same solvent in which the copolymer was prepared or may be one or more different solvents. Crosslinking, or gellation time, is conveniently controlled by copolymer concentration and the amount of crosslinker added, thereby allowing adequate time for coating or for filling structures, followed by rapid cure time to provide finished product. In general, the lower the copolymer concentration or the lower the amount of crosslinker, the longer it will take for the crosslinking/gellation to occur.

Crosslinkers useful for the purposes of the present invention include, without limitation, materials that include nucleophilic groups that will undergo ring-opening reactions with azlactone functional groups. Suitable crosslinkers include primary polyamines, such as ethylenediamine, 1,3-propanediamine, 1,3-diamino-2-hydroxypropane, 1,6-hexanediamine, tris-(2-aminoethyl)amine, and the like; and polyetherpolyamines, such as 4,7,10-trioxa-1,13-tridecanediamine, 3,6-dioxa-1,8-diaminooctane, amine-terminated polyethyleneglycol and polypropyleneglycol homopolymers and copolymers, and the like. To achieve the purposes of the invention, the stoichiometry between the nucleophilic groups of the crosslinker and the azlactone functional groups of the copolymer should be less that 1:1 so that the final crosslinked hydrogel still contains reactive azlactone functionality. Thus, the azlactone content in the original copolymer will provide an upper limit on the amount of crosslinker that may be added to the coating formulation. The intended final use of the hydrogel may also dictate, to a certain degree, the amount of crosslinker used in the formulation. The amount of crosslinking will influence the swelling and porosity of the hydrogel, thus affecting the rate of diffusion of reagents or target molecules into and out of the hydrogel. Generally, less crosslinking provides a hydrogel having larger pores, thereby allowing diffusion of larger biological macromolecules through the hydrogel.

As indicated above, gellation time can be controlled to a certain extent by controlling the concentrations of copolymer and crosslinker. As used herein, gellation time refers to the amount of time necessary for a solution that can form a gel to become no longer fluid. In many instances, these parameters provide adequate control to allow placing the coating solution into the proper configuration prior to the occurrence of gellation. For some applications or product concepts, however, these parameters by themselves do not allow long enough gel times for use in manufacturing. Through the use of some novel crosslinking schemes, the present invention now provides coating formulations with extended pot lives; that is, the coating formulations remain soluble and homogeneous with low attendant viscosities for extended periods of time. Upon evaporation of the solvent and/or raising the temperature of the coated substrate, the coating formulations crosslink to produce the hydrogels of the present invention. These novel crosslinking schemes are achieved by using heterobifunctional crosslinkers, i.e., crosslinkers that have one nucleophilic functional group that reacts with the azlactone group at ambient temperature in solution (e.g., a primary amine) and at least one other functional group that can lead to a crosslinking reaction upon removal of the solvent or upon raising the temperature.

One class of crosslinkers that may be used in this manner is the aminoalkylalkoxysilanes such as, for example, 3-aminopropyltrimethoxysilane, 3-aminopropyltriethoxysilane, N-[3-(trimethoxysilyl)propyl]ethylenediamine, or other aminoalkylmono-, di- and tri-alkoxysilanes. The amino group undergoes a ring-opening addition reaction with an azlactone group, providing a pendant alkoxysilane group on the copolymer. Upon dry-down, the alkoxy groups may be hydrolyzed and subsequently form siloxane crosslinks between polymer chains. Depending upon the nature of the substrate, covalent bonds may simultaneously be made with functional groups on the surface of the substrate (for example, if the substrate is siliceous, siloxane linkages to the substrate may be formed).

Another class of crosslinking agents useful for prolonging pot life or gellation times includes primary/secondary (1°/2°) amine-containing compounds. In these materials, the primary amine provides rapid reaction with an azlactone group on the copolymer at room temperature, while the secondary amine is relatively slow to react. Removing the solvent, raising the temperature of the coated article, or both allows the secondary amine to react to form the hydrogel. Suitable 1°/2° amine-containing compounds include, without limitation, N-methyl-1,2-ethanediamine, N-ethyl-1,2-ethanediamine, N-isopropyl-1,2-ethanediamine, and other N-alkyldiaminoalkanes. Increasing the steric bulk of the N-alkyl substituent provides a greater barrier to reaction of the secondary amino group, thus necessitating a higher temperature to produce crosslinking.

Once formulated, the coating solutions can be applied to desired substrates and dried (optionally with the application of heat) to produce the hydrogels of the present invention. Coating methods can vary widely depending upon the particular substrate, and may be selected from methods known in the art. These include, for example, extrusion coating, die coating, dip coating, air-knife coating, gravure coating, curtain coating, spray coating, use of wire-wound coating rods, and the like.

With certain substrates, the hydrophilic azlactone-functional polymer will exhibit fairly good adhesion. Crosslinking to produce a hydrogel insolubilizes the coating and reduces the likelihood of the coating coming off of the substrate in subsequent manipulations. Adhesion of the coating to the substrate may be improved, if desired, by any known method. Such methods include, but are not limited to, various pre-treatments to or coatings on the surface of the substrate, such as corona or plasma treatments, or by the application of primers. Suitable primers include, without limitation, polyethylenimine, polyvinylidenechloride, primers such as those reported in U.S. Pat. No. 5,602,202, issued to Groves, and colloidal dispersions of inorganic metal oxides in combination with ambifunctional silanes such as those reported in U.S. Pat. No. 5,204,219, issued to Van Ooij et al., 5,464,900, issued to Stofko et al., and 5,639,546, issued to Bilkadi. Other methods of increasing adhesion to polyolefin substrates are reported in U.S. Pat. No. 5,500,251, issued to Burgoyne et al.

The hydrophilic coatings and hydrogels of the invention may be applied to a wide variety of substrates. The substrates may be natural or synthetic, organic or inorganic, porous or nonporous, flat and substantially featureless or highly structured. The substrates may be film-like, particulate-like, or molded plastic articles. Suitable substrates include, without limitation, standard 96-, 384-, or 1536-well plastic microtiter plates, including filtration plates; grooved, microreplicated films; microfluidic channels in microfluidic devices; embossed or microstructured films; tubes or capillaries; spin tubes or spin columns; glass, ceramic, or metal particles or fibers, including porous particles or fibers; porous or nonporous polymeric fibers or particles, such as chromatographic particles; oriented or non-oriented polymeric films; woven or nonwoven webs (such as fibrous webs); porous or microporous membranes; and the like.

The substrate chosen will depend upon the intended application or device. Those applications include, without limitation, devices such as DNA or protein arrays; biological assay or diagnostic devices; capillary electrophoresis, electrochromatography, or other separation devices; chromatographic supports for affinity, ion exchange, hydrophobic interaction, or other types of separations and purifications; cell selection or separation devices; and the like. For example, when using oriented polymeric films as the substrate, the coatings of the invention are advantageously used to prepare high-density, miniaturized arrays as described in International Publication Number WO 99/53319.

Once the reactive coatings or hydrogels are applied to the substrates, the residual azlactone functionality is available for reaction with the functional material. Again, the intended application will dictate the identity of the functional material. Preferred functional materials are biologically active materials such as proteins, enzymes, oligonucleotides, or any other species that may interact with biological species. Derivatization may be conducted in aqueous, buffered media, as is well known for reactions of azlactone-functional substrates, although other media such as organic solvents may be used.

EXAMPLES

The following examples have been selected merely to further illustrate features, advantages, and other details of the invention. It is to be expressly understood, however, that while the examples serve this purpose, the particular ingredients and amounts used as well as other conditions and details are not to be construed in a matter that would unduly limit the scope of this invention.

Example 1

Gel Formation in Microtiter Tray Format

40% Solids solutions in methyl ethyl ketone (MEK) of 90:10 w/w and 70:30 w/w copolymers of dimethylacrylamide (DMA) and vinyldimethylazlactone (VDM) were prepared by standard free radical polymerization techniques. Portions of each were diluted with 20:1 v/v isopropanol: MEK to give solutions of 2.5% and 10% solids of each copolymer. Portions of each of these dilute solutions were then formulated with enough aminopropyltrimethoxysilane to react with and provide crosslink densities of 2.5% and 10% by weight, thus providing a total of 8 different formulations. These solutions were then deposited, using a micropipette, into the wells of a 384-well polypropylene microtiter tray. Some of the wells were left exposed to the ambient atmosphere while others were covered with Scotch Brand Magic Mending Tape (Minnesota Mining and Manufacturing Co., St. Paul, Minn.). The mixtures in the wells were observed to thicken and become gelled (crosslinked). Shrinkage was observed in the untaped wells due to solvent loss, however, swelling reoccurred upon addition of solvent or water. Upon removal of the tape from the taped wells, the gels were smoothly pulled out of the wells and remained tightly adhered to the tape in a raised gel pattern. Except for the gels prepared from 90:10 poly(DMA/VDM)/10% crosslinker, all have residual azlactone functionality which can be used for covalent attachment of biological or other functional materials.

Example 2

Formation of Gels in 96-Well Plate

The formulations of Example 1 were used to fill wells (250 microliters each) in a commercial polystyrene 96-well microtitration plate. Because of the larger volume, longer gellation times were observed. Some of the gels could be pulled from the wells with tape as described in Example 1. Alternatively, addition of smaller amounts of solution, or of lower % solids solutions, allowed formation of thin coatings of azlactone-functional hydrogels on the interior surfaces of the microwells.

Example 3

Formation of Reactive Coating within Wells of a 1536-Well Plate

A 40% solids solution (MEK) of 80:20 w/w poly(DMA/VDM) was diluted to 20% solids with isopropanol (IPA), formulated with enough ethylenediamine to provide a crosslink density of about 10% by weight, then applied to a commercial 1536-well plate. A windshield wiper blade was used to coat and force the solution into the wells. Upon drying, a reactive, azlactone-functional polymeric coating was obtained within the wells.

Example 4

Formation of Thin, Reactive Coating in a Microtiter Tray

A portion of polypropylene 384-well microtiter tray was cleaned by rinsing with methanol and isopropanol, then dried in an oven at 50° C. for 5 minutes. 1 µl, 2 µl, 3 µl, 4 µl, 5 µl or 10 µl of 0.1% w/w polyethylenimine in deionized water were added to adjacent wells in each of two separate rows. A third row of wells was left untreated. The tray was dried in the oven again for 5 minutes. 2 microliters of 5% solids 70:30 poly(DMA/VDM) copolymer, prepared as in Example 1, was added to each well. The tray was again oven-dried for 5 minutes. A solution of 5-((5-aminopentyl) thioureidyl) fluorescein cadaverine (1 mg/ml in dimethylformamide, Molecular Probes, Inc., Eugene, Oreg.) was diluted to a concentration of 20 micrograms/ml using a buffer consisting of 1 M sodium sulfate in 50 mM 3-[(1,1-dimethyl-2-hydroxyethyl)amino-2-hydroxypropanesulfonic acid (AMPSO), pH 9.0, in deionized water. 2 microliters of this dilute dye solution was added to each of the coated wells and allowed to dry. The tray was then washed thoroughly with deionized water, wetted with some of the above AMPSO buffer, and observed under short wavelength (254 nm) UV irradiation. All wells were examined for fluorescence. Green fluorescence within a well indicated that the fluorescein cadaverine had reacted with the azlactone copolymer coating and had become covalently bound within the well. The tray was then washed with the AMPSO buffer and reexamined. No fluorescence was observed in the untreated wells, indicating that the coating had not adhered to the copolymer and had been washed off with the AMPSO buffer. However, all wells primed with polyethylenimine still showed fluorescence, with the intensity increasing with increasing PEI level. The tray subsequently was washed with 1% w/w SDS (sodium dodecylsulfate) in deionized water and reexamined. No change was seen, indicating good adhesion and/or the PEI priming accomplished crosslinking.

The above experiment was repeated using a microtiter tray containing larger (ca. 8 mm×8 mm square) wells, and larger volumes of the various solutions. Similar results were observed.

Example 5

Effect of Solvent, Concentration, and Crosslinker on Gel Time

The 70:30 w/w p(DMA/VDM) copolymer from Example 1 (Polymer A), prepared at 40% solids in MEK, was determined by gel permeation chromatography (GPC) to have a weight average molecular weight ($M_w$) of 600,000. A similar copolymer (Polymer B) was prepared at 40% solids in toluene, and determined to have a $M_w$ of 702,000. These two copolymer solutions were diluted with either methyl ethyl ketone (MEK) or isopropanol (IPA) to concentrations varying from 5–15% solids, then formulated with enough ethylenediamine to react with 1–10% by weight of the total monomer units in the copolymer. Gellation times (time at which the solution was no longer fluid) were observed. Results are listed in Table 1.

TABLE 1

Hydrogel Formation

| Polymer | % Solids | Diluent | % ED | Gel Time |
|---|---|---|---|---|
| A | 10 | IPA | 1 | 84 min |
| A | 10 | IPA | 2.5 | 50 min |
| A | 10 | IPA | 5 | 27 min |
| A | 10 | IPA | 10 | 25 min |
| A | 15 | IPA | 1 | 30 min |
| A | 15 | IPA | 2.5 | 18 min |
| A | 15 | IPA | 5 | 16 min |
| A | 15 | IPA | 10 | 13 min |
| B | 5 | IPA | 10 | 30 min |
| B | 10 | IPA | 10 | 2.25 min |
| B | 5 | MEK | 10 | >48 hrs |
| B | 10 | MEK | 10 | 60 min |

These results illustrate control of gellation times and also demonstrate the inhibitory effect of MEK on the formation of crosslinked hydrogels.

Copolymer B was diluted with IPA to give polymer concentrations of 50 mg/ml and 100 mg/ml of solution, respectively. Samples of each solution (3 ml each) were formulated with enough diamine to provide 10% and 20% crosslinking. Diamines utilized were N-ethyl-1,2-ethanediamine, N-propyl-1,2-ethanediamine, and N-isopropyl-1,2-ethanediamine (N-EED, N-PED, and N-IED, respectively). Gellation times were observed at room temperature and at 65° C. No gellation was observed at room temperature over several days. At 65° C., gel times occurred in the following order: N-EED (fastest)>N-PED>N-IED. In a separate experiment, an IPA solution of copolymer B/10% N-EED was dried down at room temperature; the dry polymer readily re-dissolved upon addition of solvent. By contrast, a sample dried at 65° C. would not redissolve, indicating that crosslinking had occurred at the elevated temperature. Infrared spectroscopy verified the extent of reaction with various crosslinkers by comparing the intensity of the azlactone carbonyl absorption band at about 1820 cm$^{-1}$ to the amide carbonyl band at about 1640 cm$^{-1}$. All of these results illustrate that secondary amines can be used to control the rate of crosslinking reactions with azlactone functional groups.

Example 6

Additional Experiments on Gel Formation

Numerous experiments were conducted on the formation of gels using microcentrifuge tubes as containers. Various polymer solutions were prepared varying from 1.0% solids to 20% solids, then these were reacted with a variety of crosslinkers (using varying amounts of each separate crosslinker), and the gellation times noted. Copolymer solutions used included:
  a) 95:5, 90:10, and 70:30 w/w p(Acrylamide/VDM) in water;
  b) 80:20 w/w poly(DMA/VDM) in isopropanol Crosslinkers Included:
  a) Aminopropyltrimethoxysilane
  b) 1.0 M ethylenediamine in ethanol
  c) 10% w/w PEI in methanol
  d) Polylysine in water Gellation times of minutes to hours after mixing were obtained, and could be controlled by varying polymer % solids and amount of crosslinker added. These same variables affected the stiffness of the gel that formed.

Example 7

Coating of Microreplicated Films

A microreplicated polypropylene film approximately 5.5 cm wide, containing 25 channels approximately 1 mm×1 mm in cross-sectional dimensions, spaced 1 mm apart, and running the length of the film, was used as the substrate. Several coating solutions of Polymer A similar to those described in Example 5 were prepared (varying from 1–15% solids and containing 1–10% crosslinker), and were applied by syringe into channels of the substrate. After the coating was crosslinked and dried, the coated substrate was placed in deionized water to rehydrate the gels. In many instances, the gels were observed to swell and pop out of the channels, thereby indicating poor adhesion to the substrate. To minimize this problem, the substrate was primed by dip coating in a 1% w/w solution of polyethylenimine (PEI) in methanol followed by drying at ambient temperature overnight. New coating solutions at 5% and 10% solids with 2.5%, 5%, and 10% crosslinker were applied and allowed to gel. The gels were observed to remain in the channels when challenged with deionized water, even though they did swell somewhat.

Example 8

Immobilization of Proteins on Microreplicated Films

The PEI-primed substrate of Example 7 was used, and channels were filled with gels derived from 5% solids copolymer formulated with 5% ethylenediamine as crosslinker. Separate pieces of coated substrate were individually dipped in the following protein coupling solutions for 30 minutes to 1 hour: (a) 5 mg/ml bovine serum albumin in phosphate buffered saline (PBS), pH 7.5, containing 1.0 M sodium sulfate; (b) 5 mg/ml myoglobin in 0.1 M 2-[N- cyclohexylamino]ethanesulfonic acid (CHES), pH 9.0, containing 1.0 M citrate; (c) 1 mg/ml Protein A in PBS, pH 7.5, containing 0.9 M sodium sulfate. After coupling, the substrates were washed thoroughly with 1.0 M sodium chloride in PBS to remove any noncovalently bound protein.

Protein Coupling was Evaluated as Follows:

(a) A coated substrate was reacted with myoglobin, coupled as described above, and then observed with an optical microscope. The coated substrate contained reddish-brown stained gels in the channels, indicative of coupled myoglobin.

(b) A coated substrate was reacted with myoglobin and placed in a solution of BCA protein assay reagent (Pierce Chemical Co., Rockford, Ill.). The formation of a deep purple color indicated the presence of coupled protein.

(c) A coated substrate that had been reacted with Protein A and a coated substrate that had been reated with albumin were separately soaked in dilute solutions of rabbit IgG FITC (fluorescein isothiocyanate) conjugate (Sigma Chemical Co., St. Louis. Mo.) in PBS. The coated substrates were washed with PBS, then observed microscopically for bound fluorescence. The coated substrate that had been reacted with Protein A exhibited a strong fluorescent signal, thereby indicating that the IgGs had bound to the Protein A. The coated substrate that had been reacted with albumin exhibited no fluorescence. When the fluorescence intensity of the Protein A coupled gel was measured using a raster scanning device equipped with a 488 nanometer laser, fluorescein filters, and a photomultiplier tube, the intensity was found to be 74,300 RLU (relative light units) above background (uncoated plastic). Control samples that had not been exposed to proteins also exhibited no bound fluorescence.

Similar results were obtained when these experiments were repeated on a microreplicated film having much smaller "V groove" channels. These microchannels had a triangular cross section with a base of approximately 0.3 mm and a height of approximately 0.35 mm.

Example 9

Coating Glass Slides with Azlactone Polymers

Azlactone/dimethylacrylamide copolymer was premixed with 3-aminopropyltrimethoxysilane (APTMS) and then coated onto glass slides. The amino group of the APTMS is able to react with an azlactone group on the copolymer and the trimethoxysilyl (TMS) group of the APTMS is able to react with the glass. Also some of the TMS groups will react with other TMS groups, thereby resulting in crosslinking.

Glass Slide Preparation:

Frosted-ended glass slides were placed in 1 M sodium hydroxide and allowed to soak for 10 minutes. The slides were removed with forceps and washed under a stream of distilled water to remove all excess sodium hydroxide. The slides were then dipped in 1M HCl and soaked for at least 10 minutes with gentle rocking or occasional stirring. Finally, the slides were washed in a stream of distilled water to remove all of the HCl, rinsed with methanol, and placed in an oven to dry (50°–70° C.).

Solutions:
1. Polymer Solvent: 20:1 IPA:MEK (200 mL IPA and 10 mL MEK)
2. Polymer solutions: A stock solution of 50:50 w/w DMA/VDM copolymer, prepared at 40% solids in MEK, was diluted to 2%, 5% and 10% solids using the Polymer Solvent.
3. APTMS: This reagent was used undiluted or as a 1:10 dilution in Polymer Solvent. Just before use, 1 ml of APTMS was mixed with 9 ml of the Polymer Solvent and kept in a sealed glass vial.
4. Fluorescein cadaverine: 100 μg/mL of fluorescein cadaverine in a solution of 1M sodium sulfate in 50 mM AMPSO buffer at pH 9.5.

Slide Coating:

The coating solutions were prepared, as shown in Table 2, just before coating. Two slides were coated with each of the listed solutions, and one cleaned slide was kept as a blank (13 slides in all). Coating was accomplished with a number 14 wire-wound coating rod. Coated slides were dried in the oven at 50° C. for 10 minutes or until completely dry.

TABLE 2

| Coating Solutions | 2% copolymer (ml) | 5% copolymer (ml) | 10% copolymer (ml) | Undiluted APTMS (μl) | 1:10 diluted APTMS (μl) |
|---|---|---|---|---|---|
| B1: 2% copolymer, 5% crosslinker | 10 | | | | 140 |
| B2: 2% copolymer, 10% crosslinker | 10 | | | | 280 |
| B3: 5% copolymer, 5% crosslinker | | 10 | | | 350 |
| B4: 5% copolymer, 10% crosslinker | | 10 | | 70 | |
| B5: 10% copolymer, 5% crosslinker | | | 10 | 70 | |
| B6: 10% copolymer, 10% crosslinker | | | 10 | 140 | |

Reaction with the Fluorescein Cadaverine:

To verify the presence of reactive azlactone functionality, coated slides were evaluated by reaction with fluorescein cadaverine. A water-soaked piece of filter paper was placed in the bottom of each of 13 petri dishes. Each coated slide was placed in a separate petri dish on top of the wet filter paper with the coated side up. Onto each slide were placed two spots each of 2 μl, 5 μl, and 7 μl of the fluorescein cadaverine solution, being careful to keep the spots separated. Each of the petri plates were then covered and allowed to stand overnight at ambient temperature. Each slide was washed well with deionized water, followed by a solution of 5% SDS, deionized water, and finally with AMPSO buffer at pH 9.5. After washing, all slides were examined under the microscope, noting intensity of the fluorescence and quality of the adhesion to the substrate. All formulations exhibited good binding of the fluorescent amine, however B1, B3, and B5 did not display as good adhesion as the other formulations. The blank showed no fluorescence.

Example 10

Example 9 was repeated using the 70:30 w/w poly(DMA/VDM) copolymer of Example 1. In this case, all formulations exhibited excellent adhesion and dye binding, while the blank again showed no fluorescence.

Example 11

Example 10 was repeated using polycarbonate film as the substrate instead of glass slides. Results were similar to those observed in Example 10.

Example 12

Coating of Particulate Substrates

A 70:30 w/w copolymer of DMA and VDM similar to Polymer B of Example 5 (0.9 g of a 22.3% solids solution in isopropanol/toluene) was diluted to 25.5 ml with IPA to give a 1% solids solution. Ethylenediamine (4.8 µl) was added to provide 10% crosslinking. The resulting solution was mixed in a round bottomed flask with 5.0 g POROS 50-R2 (porous, crosslinked styrene-divinylbenzene chromatographic beads from PerSeptive Biosystems, Inc., Framingham, Mass.). The mixture was placed on a rotary evaporator and concentrated to dryness under vacuum. Diffuse reflectance infrared analysis of the coated particles showed absorbances at about 1650 and 1820 $cm^{-1}$, indicative of the amide and azlactone carbonyl stretches of the copolymer, respectively.

A protein coupling solution consisting of 5 mg/ml myoglobin in 0.1 M CHES, pH 9.0, containing 1.0 M citrate and 0.1% by weight TWEEN 20 detergent was prepared. 30 mg of coated beads were mixed with 5 ml of protein solution. In a separate reaction, 30 mg of coated beads were pre-wet with 0.1 ml of methanol prior to the addition of protein solution. Beads were allowed to react with the protein coupling solution with end-over-end mixing for 1 hour. 1% SDS solution (3 ml) was added to each reaction and mixing was continued for an additional 30 minutes. The mixtures were centrifuged and the absorbance of the supernates was measured at 532 nm and compared to a standard prepared by mixing 5 ml of protein solution with 3 ml SDS solution. From the supernate absorbances, the beads in the first experiment were calculated to have coupled 27.9 mg myoglobin per gram of bead, whereas beads in the presence of methanol coupled 38.0 mg myoglobin per gram of bead. A control, uncoated bead exhibited no coupling of myoglobin.

In analogous experiments, porous and nonporous silica beads were coated with azlactone functional copolymers using either ethylenediamine or APTMS as crosslinkers.

Example 13

Coating of Nonwoven Webs

A variety of nonwoven webs were coated with hydrogels derived from a 70:30 w/w poly(DMA/VDM) prepared by free radical polymerization in IPA and crosslinked at the 10 wt. % level with either ethylenediamine (ED) or N-ethylethylenediamine (N-EED). The copolymer was diluted to either 1.5% or 3.0% solids with IPA prior to formulation with the crosslinker. Nonwovens used were commercial samples of spunbond nylon (Nylon), polybutyleneterephthalate (PBT), polyethyleneterephthalate (PET), or polypropylene (PP). Samples of the nonwoven were soaked in coating solution for 30 minutes, patted dry with a wipe (Texwipe Co., Upper Saddle River, N.J.), and dried in an oven at 50° C. for 30 minutes. Following coating, the amount of available azlactone functional groups was determined by converting the azlactones to primary amines, then measuring the amine content using a commercial ninhydrin assay kit (Applied Biosystems Corp., Foster City, Calif.) according to the manufacturer's instructions. For this assay, a weighed sample of the coated nonwoven was allowed to react with a 0.5 M solution of ED in IPA for 30 minutes, then washed successively with 3–15 ml portions each of dimethylformamide, deionized water, and ethanol prior to beginning the ninhydrin assay. Results are listed in Table 3.

TABLE 3

Functionality of Coated Nonwovens

| Example | Nonwoven | Web density (g/m$^2$) | % Solids | Crosslinker | Amine Content (nmol/mg) |
|---|---|---|---|---|---|
| 13a | Nylon | NA | 3.0 | ED | 21 |
| 13b | PBT | 41.2 | 3.0 | ED | 93 |
| 13c | PET | 35.0 | 3.0 | ED | 104 |
| 13d | PP | 15.0 | 1.5 | ED | 69 |
| 13e | PP | 15.0 | 3.0 | ED | 148 |
| 13f | PP | 15.0 | 1.5 | N-EED | 47 |
| 13g | PP | 15.0 | 3.0 | N-EED | 93 |

Example 14

Coating of Oriented Polymer Films

Coating of the compositions of the present invention on biaxially oriented polyethylene film for the purposes of preparing miniaturized arrays is reported in International Publication Number WO 99/53319.

A substrate film was corona treated according to known techniques prior to coating. The substrate was coated by extrusion die coating with 70:30 w/w poly(DMA/VDM, with 10% 1,2-ethylenediamine (Aldrich Chemical Co., Milwaukee, Wis.) by weight as crosslinker, prepared and diluted with isopropanol. Another substrate was treated and coated similarly, except that the coating was prepared and diluted in methyl ethyl ketone. Each substrate was tested for stability as follows.

A 50 mM sodium phosphate buffer was prepared at pH 8.38 with 1% (w/w) sodium dodecyl sulfate (SDS) in deionized water. The substrates were immersed in the buffer solution at 80° C. for 5 hours. The substrates were analyzed using attenuated total reflectance (ATR) IR spectroscopy to detect presence of the coating.

The coating prepared in isopropanol provided better adhesion than the coating prepared in methyl ethyl ketone. Even better stability, even prior to relaxation of the substrate, is obtained by applying IPA-based coatings to metal coated oriented films such as those described in International Publication Number WO 01/16370.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An article comprising:
   a substrate; and
   a material disposed upon the substrate, the material comprising
   i) at least one azlactone-functional copolymer comprising a plurality of azlactone moieties and a plurality of azlactone functional groups, wherein the copolymer is derived from monomers comprising at least one alkenyl azlactone monomer and at least one hydrophilic or water soluble comonomer;

ii) a first crosslinker comprising a first nucleophilic moiety and a second thermally reactive moiety; and iii) optionally, a second crosslinker comprising a first nucleophilic moiety and a second thermally reactive moiety;

wherein a) the first moiety of a first crosslinker is covalently bound to a first azlactone moiety; and b) the second moiety of the first crosslinker is covalently bound to i) a second azlactone moiety or ii) the second moiety of the second crosslinker, with the first moiety of the second crosslinker being bound to the second azlactone moiety; and wherein the material is a crosslinked hydrogel.

2. The article of claim 1 wherein the substrate comprises a plate, a film, a particle, a fiber, a column, a bead, a web, or a membrane.

3. The article of claim 1 further comprising a primer.

4. The article of claim 3 wherein the primer is polyethylenimine, polyvinylidene chloride, a colloidal dispersion of metal oxides, or an ambifunctional silane.

5. The article of claim 1 wherein the first crosslinker and the second crosslinker have the same chemical structure.

6. The article of claim 1 wherein the first crosslinker and the second crosslinker have different chemical structures.

7. The article of claim 1 wherein the chemical structure of the second moiety of the first crosslinker is the same as the chemical structure of the first moiety of the first crosslinker.

8. The article of claim 1 wherein the chemical structure of the second moiety of the first crosslinker is different than the chemical structure of the first moiety of the first crosslinker.

9. The article of claim 1 wherein the chemical structure of the second moiety of the second crosslinker is the same as the chemical structure of the first moiety of the second crosslinker.

10. The article of claim 1 wherein the chemical structure of the second moiety of the second crosslinker is different than the chemical structure of the first moiety of the second crosslinker.

11. A composite comprising:

(a) a substrate;

(b) a hydrogel material disposed upon the substrate wherein the hydrogel material comprises:

i) at least one azlactone-functional copolymer comprising a plurality of azlactone moieties and a plurality of azlactone functional groups, wherein the copolymer is derived from monomers comprising at least one alkenyl azlactone monomer and at least one hydrophilic or water soluble comonomer;

ii) a first crosslinker comprising a first nucleophilic moiety and a second thermally reactive moiety; and iii) optionally, a second crosslinker comprising a first nucleophilic moiety and a second thermally reactive moiety;

wherein:

a) the first moiety of the first crosslinker is covalently bound to a first azlactone moiety; and b) the second moiety of the first crosslinker is covalently bound to i) a second azlactone moiety or ii) the second moiety of the second crosslinker, with the first moiety of the second crosslinker being bound to the second azlactone moiety; and wherein the hydrogel material is a crosslinked hydrogel; and (c) a functional material comprising (i) a nucleophilic group reacted with a third azlactone moiety of the azlactone-functional copolymer and (ii) another reactive site.

12. The composite of claim 11 wherein the substrate comprises a plate, a film, a particle, a fiber, a column, a bead, a web, or a membrane.

13. The composite of claim 11 further comprising a primer.

14. The composite of claim 13 wherein the primer is polyethylenimine, polyvinylidene chloride, a colloidal dispersion of metal oxides, or an ambifunctional silane.

15. The composite of claim 11 wherein the functional material is a polypeptide, a polynucleotide, a polysaccharide, or any combination thereof.

16. The composite of claim 11 wherein the first crosslinker and the second crosslinker have the same chemical structure.

17. The composite of claim 11 wherein the first crosslinker and the second crosslinker have different chemical structures.

18. The composite of claim 11 wherein the chemical structure of the second moiety of the first crosslinker is the same as the chemical structure of the first moiety of the first crosslinker.

19. The composite of claim 11 wherein the chemical structure of the second moiety of the first crosslinker is different than the chemical structure of the first moiety of the first crosslinker.

20. The composite of claim 11 wherein the chemical structure of the second moiety of the second crosslinker is the same as the chemical structure of the first moiety of the second crosslinker.

21. The composite of claim 11 wherein the chemical structure of the second moiety of the second crosslinker is different than the chemical structure of the first moiety of the second crosslinker.

22. The composite of claim 11 wherein the functional material comprises a biologically active material.

* * * * *

UNITED STATES PATENT AND TRADEMARK OFFICE
CERTIFICATE OF CORRECTION

PATENT NO. : 7,101,621 B2
APPLICATION NO. : 10/896664
DATED : September 5, 2006
INVENTOR(S) : Louis C. Haddad It is certified that error appears in the above-identified patent and that said Letters Patent is hereby corrected as shown below:

Col. 4
Line 10, delete "fictional" and insert -- functional --, therefor.
Line 49, after "merx100." delete "molecular weight of the monomer".

Col. 8
Line 51, delete "1 M" and insert -- 1M --, therefor.
Line 51, delete "3-[(1,1-" and insert -- 3-(1,1- --, therefor.

Col. 11
Line 17, delete "reated" and insert -- reacted --, therefor.
Line 51, delete "1 M" and insert -- 1M --, therefor.

Col. 13
Line 12, delete "PerSeptive" and insert -- Perseptive --, therefor.

Signed and Sealed this

Twelfth Day of June, 2007

JON W. DUDAS
*Director of the United States Patent and Trademark Office*